United States Patent [19]
Wengrovius

[11] Patent Number: 4,788,170
[45] Date of Patent: Nov. 29, 1988

[54] METHOD FOR PREPARING TIN COMPLEX CURING CATALYST

[75] Inventor: Jeffrey H. Wengrovius, Scotia, N.Y.

[73] Assignee: General Electric Company, Schenectady, N.Y.

[21] Appl. No.: 70,263

[22] Filed: Jul. 6, 1987

[51] Int. Cl.$^4$ .............................................. B01J 31/12
[52] U.S. Cl. ................................... 502/152; 502/150; 502/153; 502/158
[58] Field of Search ................ 502/150, 152, 153, 158

[56] References Cited
U.S. PATENT DOCUMENTS 4,517,337  5/1985  Lockhart et al. .................... 524/859

*Primary Examiner*—Patrick P. Garvin
*Assistant Examiner*—George R. Fourson
*Attorney, Agent, or Firm*—William H. Pittman; James C. Davis, Jr.; James Magee, Jr.

[57] ABSTRACT

Catalysts containing tin complexes such as dibutyltin bis(acetylacetonate), useful as curing catalysts for room temperature vulcanizable compositions, are prepared by the reaction of a dialkyltin oxide with a dione and a polyalkoxysilane at a temperature in the range of about 20°–80° C. At least 2 moles of dione and preferably at least 2 moles of polyalkoxysilane are employed per gram-atom of tin. The polyalkoxysilane removes water of reaction, driving the reaction to completion.

12 Claims, No Drawings

METHOD FOR PREPARING TIN COMPLEX CURING CATALYST

This invention relates to the preparation of tin complexes, and more particularly to the preparation of complexes useful as curing catalysts for room temperature vulcanizable compositions.

Considerable attention has been directed in recent years to the development of improved one-package room temperature vulcanizable (hereinafter sometimes designated "RTV") compositions. Under ideal conditions, these compositions would be stable for an indefinite period when stored in the absence of moisture, and would promptly cure to a tack-free elastomer upon contact with moisture, including the relatively small proportions of water vapor present in the atmosphere.

In a typical RTV composition, the predominant constituent is a polydiorganosiloxane (hereinafter sometimes designated "silicone" for brevity) containing polyalkoxysilyl end groups, typically dialkoxyalkylsilyl groups. These groups may be formed in situ by incorporating in the RTV composition a silanol-terminated silicone and, as an endcapping reagent, a polyalkoxysilane such as methyltrimethoxysilane, which undergo reaction to produce the polyalkoxysilyl-terminated species; or a previously formed polyalkoxysilyl-terminated silicone, prepared by the same reaction, may be employed.

In either case, the polyalkoxysilyl-terminated species is capable of being crosslinked by atmospheric moisture in the presence of a suitable metal-containing catalyst. Disclosures of RTV compositions of this type are present in many patents and publications.

The one-package RTV composition disclosed in U.S. Pat. No. 4,517,337 employs a tin complex catalyst such as dibutyltin bis(acetylacetonate), which is stable in the presence of hydroxy species such as methanol and silanol-terminated silicones and may therefore be employed without scavengers for hydroxy groups. The tin complex catalysts are prepared by the known reaction of a dione such as acetylacetone with a dialkyltin oxide. Water is generated in the reaction and its removal assists in driving the reaction to completion.

In a commonly employed method for preparing such tin complexes, the dialkyltin oxide and dione are heated in the presence of a relatively high-boiling diluent which forms an azeotrope with water. Toluene is an example of such a diluent. It is then possible to remove water by azeotropic distillation, followed by vacuum evaporation of the solvent. The tin complex is then ordinarily dissolved in a polyalkoxysilane. The resulting solution is particularly useful as an RTV curing catalyst, since polyalkoxysilanes are commonly employed in RTV compositions. However, the method of catalyst preparation is complex because of the necessity for distillation and solvent removal operations followed by dissolution in the polyalkoxysilane.

The present invention provides a simplified method for preparing tin complex RTV curing catalysts. Said method requires substantially less operations than methods known in the art, and is capable of producing a catalyst composition which furnishes several of the desired catalyst ingredients.

The invention is a method for preparing a catalyst comprising a tin complex which comprises effecting reaction, at a temperature in the range of about 20°–120° C., between the constituents of a mixture comprising:

(A) at least one dialkyltin oxide;
(B) at least 2 moles, per gram-atom of tin in reagent A, of a dione of the formula

wherein each of $R^1$, $R^2$ and $R^3$ is independently hydrogen, $R^4$, $Si(R^4)_3$, acyl or nitrile and $R^4$ is an unsubstituted or substituted hydrocarbon radical containing from 1 to about 18 carbon atoms, and (C) at least 1 mole, per gram-atom of tin in reagent A, of at least one polyalkoxysilane;

whereby water formed in the reaction between reagents A and B is removed by reaction with reagent C.

The dialkyltin oxides used as reagent A in the method of this invention may be represented by the formula

wherein $R^4$ is as previously defined. The $R^4$ radicals are usually unsubstituted. Alkyl radicals, especially those containing about 2–8 carbon atoms, are preferred, with n-butyl and n-octyl radicals being most preferred. Formula II, while stoichiometrically substantially accurate, may be a structural oversimplification by reason of the possible presence of higher condensates.

Reagent B, the dione, is represented by formula I wherein the $R^{1-3}$ radicals are as previously defined. Most often, $R^1$ and $R^3$ are alkyl radicals, especially methyl, and $R^2$ is hydrogen. Thus, the preferred dione is acetylacetone.

The polyalkoxysilane employed as reagent C may be represented by the formula

wherein $R^5$ is an unsubstituted or substituted hydrocarbon radical containing from 1 to about 13 carbon atoms, $R^6$ is an alkyl, alkoxyalkyl, acylalkyl, acyloxyalkyl or cyanoalkyl radical containing from 1 to about 8 carbon atoms or an aralkyl radical containing from 1 to about 14 carbon atoms, and a is 0 or 1. Illustrative $R^5$ radicals are methyl, ethyl, phenyl, trifluoropropyl and vinyl. Alkyl radicals having up to about 4 carbon atoms and especially methyl radicals are preferred. $R^6$ may be alkyl or the designated substituted alkyl radicals containing aryl, ethyl, ester, ketone or cyano substituents; it is also most often $C_{1-4}$ alkyl and especially methyl. The value of a is 0 or 1, most often 1. Illustrative compounds of this type are methyltrimethoxysilane (which is usually preferred), methyltriethoxysilane, ethyltrimethoxysilane, tetraethoxysilane and vinyltrimethoxysilane.

At least 2 moles of reagent B are used per gram-atom of tin in reagent A, since the tin complex catalyst contains two dione-derived moieties per tin atom. It is generally preferred to use an excess of reagent B.

The proportion of reagent C is at least 1 mole per gram-atom of tin in reagent A. This amount of reagent C is necessary since one molecule of water is evolved per tin atom. Said molecule of water reacts with the polyalkoxysilane of formula III to form one molecule of an alkanol and silanol species as possible intermediates.

The silanol species may interreact by generating another molecule of alkanol and a higher molecular weight silane, and/or by condensing with the expulsion of a molecule of water. Both products are relatively easy to handle. However, it is preferred that at least about 2 moles of reagent C be present, since it will then react with any hydroxysilane, the lowest silanol species, to produce a disiloxane and an alkanol. The overall reaction may be expressed as follows:

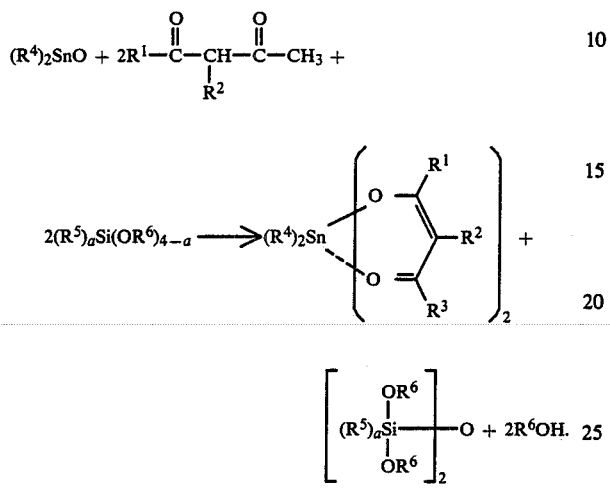

If less than 1 mole of reagent C is present per gram-atom of tin, further condensation reactions may take place to form transient polyhydroxysilyl species. These may then condense to form intractable gels or similar by-products which are difficult or impossible to handle.

In many instances, it is preferred that the RTV composition in which the tin catalyst is incorporated contain various proportions of reagents B and C in addition to the tin complex. Therefore, a preferred embodiment of the invention involves the use of an excess of said reagents. The ratio of moles of reagent B to gram-atoms of tin in A may, for example, be up to about 6:1 and is generally about 3–5.5:1, while an illustrative upper limit for the corresponding ratio of reagent C to reagent A is about 10:1 and the preferred range is about 7–8.5:1.

The reaction is conducted at temperatures in the range of about 20°–120° C., preferably about 60°–110° C., and is normally complete within a short period of time under conditions of gentle warming and effective agitation. The use of diluents is within the scope of the invention but is unnecessary under most conditions.

For the purposes of the invention, isolation of the tin complex catalyst from the reaction mixture is generally not necessary. The composition may be used as prepared as an RTV curing catalyst, and, as previously mentioned, also may furnish part or all of the polyalkoxysilane and dione frequently incorporated in the RTV composition.

As previously indicated, the compositions prepared by the method of this invention are useful as curing catalysts in RTV compositions. Such RTV compositions ordinarily comprise (D) at least one polyalkoxy-terminated silicone and (E) a catalytic amount of the tin complex composition.

The polyalkoxysilyl-terminated silicones useful as component D may be represented by the formula

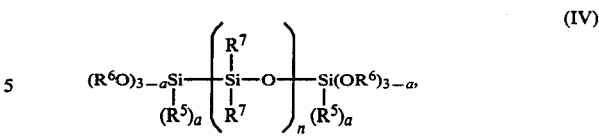

wherein $R^{5-6}$ and a are as previously defined, each $R^7$ is independently an unsubstituted or substituted hydrocarbon radical containing about 1–13 carbon atoms and m is in the range of about 5–5000. Illustrative $R^7$ radicals are methyl, ethyl, phenyl, trifluoropropyl and vinyl. Alkyl radicals having up to about 4 carbon atoms and especially methyl radicals are preferred.

Component D may be prepared in situ in the RTV composition by the reaction of a silanol-terminated silicone and, as an endcapping reagent, a polyalkoxysilane such as methyltrimethoxysilane, in accordance with U.S. Pat. No. 4,395,526. It may also be previously formed by the same reaction, most often in the presence of a catalyst as disclosed, for example, in U.S. Pat. No. 4,515,932 and copending, commonly owned application Ser. No. 90,183 filed Aug. 27, 1987. The time of its formation is not critical for the purposes of this invention, although it is frequently preferred to employ a previously formed polyalkoxylsilyl-terminated silicone.

Component E is present in the RTV compositions of this invention in an effective proportion to serve as a catalyst. In general, an amount of component E corresponding to about 0.1–10.0 parts of tin complex is employed per 100 parts of component D.

The RTV composition may also contain other constituents in common use in such compositions, including curing catalyst accelerators, scavengers for hydroxy species, adhesion promoters, plasticizers, pigments and fillers. In particular, at least one of the following may be present, all proportions being per 100 parts of component A:

(F) about 0.05–5.0 parts of a diketone of the formula

wherein $R^{1-3}$ are as previously defined;

(G) about 0.01–10.0 parts of at least one polyalkoxysilane of the formula $$(R^5)_a Si(OR^6)_{4-a}, \qquad \text{(VII)}$$

wherein $R^{5-6}$ and a are as previously defined;

(H) an effective amount, usually about 0.1–5.0 parts, of at least one adhesion promoter;

(J) about 1–50 parts of a plasticizer;

(K) about 5–700 parts of at least one filler; and (L) about 0.1–5.0 parts of an amine or guanidine as a curing accelerator.

Components F and G are often particularly preferred other constituents. Their presence contributes to the shelf stability of the RTV composition in the absence of moisture and its rapidity of cure in the presence of moisture. They are often conveniently supplied by the catalyst composition, as previously described.

Component H, the adhesion promoter, may be necessary to improve adhesion to various substrates such as aluminum and steel. Various suitable adhesion promoters, chiefly organic silicon-nitrogen compounds, are known in the the art.

The presence of component J is also frequently preferred. Suitable plasticizers useful as component J include trialkylsilyl-terminated polydiorganosiloxanes of the formula

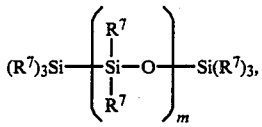
(VIII)

wherein $R^7$ is as previously defined and m is in the range of about 25–5000.

The presence or absence of component K, the filler, will depend to some extent on the intended use of the RTV composition. When the composition is to be used as a construction sealant or caulking compound, relatively large proportions of filler may be employed. For other uses, minor proportions of filler or no filler may be advisable. Suitable fillers include reinforcing materials such as silica aerogel, fumed silica, precipitated silica, glass fibers, titanium dioxide, zirconium silicate, iron oxide, calcium carbonate, diatomaceous earth and carbon black, and extending materials such as ground quartz and polyvinyl chloride, as well as mixtures thereof. It is frequently advantageous to pretreat a silica filler with an activating agent such as octamethylcyclotetrasiloxane.

Various amines and guanidines, optionally alkoxysilyl-substituted, are known to be useful as curing accelerators (component L). Suitable accelerators are disclosed, for example, in the aforementioned U.S. Pat. No. 4,517,337.

The following examples illustrate the method of this invention and the use of the resulting compositions as RTV curing catalysts. All parts are by weight.

EXAMPLE 1

A mixture of 20 parts (80.3 mmol.) of di-n-butyltin oxide, 39.1 parts (391 mmol.) of acetylacetone and 88.7 parts (651.7 mmol.) of methyltrimethoxysilane was gently warmed with vigorous stirring, whereupon it quickly became homogeneous and remained homogeneous upon cooling. The Sn-119 and Si-29 nuclear magnetic resonance spectra of the product showed the presence of di-n-butyltin bis(acetylacetone), methyltrimethoxysilane and some condensation products including dimethyltetramethoxydisiloxane.

EXAMPLE 2

An RTV composition was prepared by initially blending in a high-shear mixer 100 parts of a polymethoxysilyl-terminated polydimethylsiloxane having a Brookfield viscosity of 280 poises, 0.68 part of methyltrimethoxysilane, 16 parts of octamethylcyclotetrasiloxane-treated fumed silica and 23 parts of a trimethylsilyl-terminated polydimethylsiloxane oil having a Brookfield viscosity of 1 poise, and subsequently adding 1.25 parts of the product of Example 1 (containing 0.42 part of the tin complex, 0.28 part of acetylacetone and 1.05 parts of methyltrimethoxysilane) and 1.4 parts of tris(3-trimethoxysilylpropyl) isocyanurate. Tack-free time (TFT) values and various physical properties were determined initially and after 48 hours of heat aging at 100° C. The results are given in the following table.

|  | Before aging | After aging |
|---|---|---|
| TFT, min. | 60 | 75 |
| Shore A hardness | 17 | 17 |
| Tensile strength, millipascals | 1531 | 1186 |
| Elongation at break, % | 322 | 292 |

Adhesion-in-peel on unprimed aluminum, determined according to ASTM test method C794 after 7 days of cure at 50% relative humidity, was 145 millipascals with 80% cohesive failure.

What is claimed is:

1. A method for preparing a tin complex condensation catalyst which comprises effecting reaction, at a temperature in the range of about 20°–120° C., between the constitutents of a mixture comprising:
   (A) at least one dialkyltin oxide;
   (B) at least 2 moles, per gram-atom of tin in reagent A, of a diene of the formula

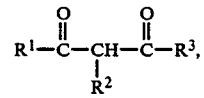

wherein each of $R^1$, $R^2$ and $R^3$ is independently hydrogen, $R^4$, $Si(R^4)_3$, acyl or nitrile and $R^4$ is a hydrocarbon radical containing from 1 to about 18 carbon atoms, and
   (C) at least 1 mole, per gram-atom of tin in reagent A, of at least one polyalkoxysilane;
   whereby water formed in the reaction between reagents A and B is removed by reaction with reagent C.

2. A method according to claim 1 wherein at least about 2 moles of reagent C is present per gram-atom of tin in reagent A.

3. A method according to claim 2 wherein $R^1$ and $R^3$ are alkyl and $R^2$ is hydrogen.

4. A method according to claim 3 wherein the ratio of moles of reagent B to gram-atoms of tin in reagent A is up to about 6:1.

5. A method according to claim 4 wherein the ratio of moles of reagent C to gram-atoms of tin in reagent A is up to about 10:1.

6. A method according to claim 5 wherein reagent B is acetylacetone.

7. A method according to claim 6 wherein reagent C is methyltrimethoxysilane.

8. A method according to claim 7 wherein the ratio of moles of reagent B to gram-atoms of tin in reagent A is about 3–5.5:1.

9. A method according to claim 8 wherein the ratio of moles of reagent C to gram-atoms of tin in reagent A is about 7–8.5:1.

10. A method according to claim 9 wherein reagent A is di-n-butyltin oxide.

11. A method according to claim 9 wherein reagent A is di-n-octyltin oxide.

12. A method according to claim 9 wherein the reaction temperature is in the range of about 60°–110° C.

* * * * *